United States Patent
Kim et al.

(10) Patent No.: US 9,073,972 B2
(45) Date of Patent: Jul. 7, 2015

(54) METHOD OF SEPARATING AND PURIFYING CELLULAR COMPONENTS USING NON-COVALENT BOND BETWEEN CUCURBITURIL DERIVATIVE AND GUEST COMPOUND AND APPARATUS USING THE SAME

(75) Inventors: Ki Moon Kim, Pohang (KR); Don Wook Lee, Seoul (KR); Sung Ho Ryu, Pohang (KR); Sang Hoon Ha, Pohang (KR); Hyun Tae Jung, Pohang (KR); Banerjee Mainak, Pohang (KR); Narayanan Selvapalam, Pohang (KR); Kyeng Min Park, Seoul (KR)

(73) Assignee: POSTECH ACADEMY-INDUSTRY FOUNDATION, Pohang-Si, Kyungsangbuk-Do (KR)

( * ) Notice: Subject to any disclaimer, the term of this patent is extended or adjusted under 35 U.S.C. 154(b) by 331 days.

(21) Appl. No.: 12/988,254

(22) PCT Filed: Apr. 15, 2009

(86) PCT No.: PCT/KR2009/001947
§ 371 (c)(1),
(2), (4) Date: Jan. 5, 2011

(87) PCT Pub. No.: WO2009/128649
PCT Pub. Date: Oct. 22, 2009

(65) Prior Publication Data
US 2011/0092680 A1    Apr. 21, 2011

(30) Foreign Application Priority Data
Apr. 16, 2008  (KR) ........................ 10-2008-0035223

(51) Int. Cl.
| | | |
|---|---|---|
| C12N 15/10 | (2006.01) | |
| C12N 9/00 | (2006.01) | |
| C07K 1/30 | (2006.01) | |
| B01J 8/00 | (2006.01) | |
| C07K 1/22 | (2006.01) | |

(52) U.S. Cl.
CPC ...................................... *C07K 1/22* (2013.01)

(58) Field of Classification Search
None
See application file for complete search history.

(56) References Cited

U.S. PATENT DOCUMENTS

| 4,539,399 A | 9/1985 | Armstrong |
| 2007/0092867 A1 | 4/2007 | Kim et al. |

FOREIGN PATENT DOCUMENTS

| EP | 1094065 A3 | 10/2001 |
| KR | 100263872 B1 | 5/2000 |
| KR | 10-2005-0005582 A | 1/2005 |
| WO | 2007046575 | 4/2007 |

OTHER PUBLICATIONS

Scheurer et al., "Identification and relative quantification of membrane proteins by surface biotinylation and two-dimensional peptide mapping," Proteomics, 2005, vol. 5, issue 11, pp. 2718-2728.*
Chruma et al., "General method for the synthesis of N-methyl amino acids and N-alkyl amino esters from O'Donnell's Schiff bases," Tetrahedron Letters, 1997, vol. 38, issue 29, pp. 5085-5086.*
A print out from Pierce Catalog retrieved from http://www.piercenet.com/browse.cfm?fldID=02040114 on Mar. 4, 2013.*
Marintcheva et al., "Acidic C-terminal tail of the ssDNA-binding protein of bacteriophage T7 and ssDNA compete for the same binding surface," PNAS, 2008, vol. 105, No. 6, pp. 1855-1860.*
International Search Report, Application No. PCT/KR2009/001947, dated Sep. 30, 2009.
Written Opinion of the International Searching Authority, Application No. PCT/KR2009/001947, dated Sep. 30, 2009.
Rekharsky, Mikhail et al., "A synthetic host-guest system achieves avidin-biotin affinity by overcoming enthalpy-entropy compensation", PNAS, vol. 104 (52): pp. 20737-20742, Dec. 26, 2007.
Padeste, C. Grubelnik, A. "Ferrocene-avidin conjugates for bioelectrochemical applications", Biosensors & Bioelectronics, 2000, vol. 15, pp. 431-438, Elsevier Science S.A.
Katherine A. Kellersberger, Joseph D. Anderson, Sarah M. Ward, Krzysztof E. Krakowiak,& David V. Dearden, "Encapsulation of N2, O2, Methanol, or Acetonitrile byDecamethylcucurbit[5]uril(NH4+)2 Complexes in the Gas Phase: Influence of the Guest on "Lid" Tightness", J. Am. Chem. Soc. 2001, vol. 123, pp. 11316-11317, American Chemical Society.
Edward L. Clennan, Robert P. L'Esperance, and Kathleen K. Lewis, "Additions of Singlet Oxygen to Alkoxy-Substituted Butadienes. An Unexpectedly Large s-Cis/s-Trans Ratio in an (E,Z)-Diene or a Kinetic Anomeric Effect?", J. Org. Chem., vol. 51, No. 9, 1986, pp. 1440-1446, American Chemical Society.

(Continued)

*Primary Examiner* — Galina Yakovleva
(74) *Attorney, Agent, or Firm* — Kile Park Reed & Houtterman PLLC

(57) ABSTRACT

Provided is a method of separating cellular components, the method including: a) contacting a guest compound-bound reactive compound with cells; b) lysing the cells; c) adding a host compound-bound solid phase to a solution including the lysates of the cells to prepare a mixture; d) separating binding pairs of the guest compound bound to cellular components and the host compound bound to the solid phase from the mixture, and purifying the binding pairs; and e) separating the cellular components from the binding pairs, wherein the guest compound-bound reactive compound is obtained through a covalent bond between a reactive compound and a guest compound represented by Formula 2 below guest, the host compound-bound solid phase is obtained through a covalent bond between a solid phase and a host compound represented by Formula 1 below, and the reactive compound includes at least one selected from the group consisting of a biomolecule, N-hydroxysuccimide, an antigen, an antibody, an aptamer, folic acid, transferrin, and any mixtures thereof.

15 Claims, 4 Drawing Sheets

(56) References Cited

OTHER PUBLICATIONS

Office Action by Japanese patent Office for Appl. No. 2011-504924, dated Jan. 14, 2014.

Ilha Hwang et al., "Noncovalent Immobilization of Proteins on a Solid Surface by Cucurbit[7]uril-Ferrocenemethylammonium Pair, a Potential Replacement of Biotin-Avidin Pair", JACS, vol. 129, No. 14, pp. 4170-4171, Feb. 16, 2007.

Japanese Office Action for Application No. 2011-504924, dated Apr. 16, 2013 and the English Translation thereof.

* cited by examiner

METHOD OF SEPARATING AND PURIFYING CELLULAR COMPONENTS USING NON-COVALENT BOND BETWEEN CUCURBITURIL DERIVATIVE AND GUEST COMPOUND AND APPARATUS USING THE SAME

TECHNICAL FIELD

The present invention relates to a method of separating and purifying cellular components, and more particularly, to a method of selectively separating and purifying cellular components using a non-covalent bond between a host compound in the form of a cucurbituril derivative and a guest compound, and an apparatus using the same.

BACKGROUND ART

Host compounds such as cyclodextrin (U.S. Pat. No. 4,539, 399) and crown ether (Korean Patent No. 0263872) can bind to various guest compounds, and thus can be efficiently used for the separation and removal of specific materials. The host compounds are covalently bound to a polymer solid substrate such as silica gel, zeolite, a titanium oxide, or cellulose to be used as a column filler. A host compound covalently bound to a solid substrate may be used as a stationary phase of a column filler in various column chromatographies for the separation of samples.

Unlike cyclodextrin, cucurbituril is a host compound forming a non-covalent bond with various hydrophilic compounds in addition to hydrophobic compounds, as guest compounds, particularly biochemical compounds substituted with amine (*J. Am. Chem. Soc.* 2001, 123, 11316; EP 1094065; *J. Org. Chem.* 1986, 51, 1440).

Thus, various compounds may be separated using a cucurbituril derivative.

DISCLOSURE OF THE INVENTION

Technical Problem

The present invention provides a method of separating and purifying cellular components using non-covalent bond between cucurbituril derivative and guest compound.

The present invention also provides an apparatus using the method.

Technical Solution

According to an aspect of the present invention, there is provided a method of separating cellular components, the method including:

a) contacting a guest compound-bound reactive compound with cells;

b) lysing the cells;

c) adding a host compound-bound solid phase to a solution comprising the lysates of the cells to prepare a mixture;

d) separating binding pairs of the guest compound bound to cellular components and the host compound bound to the solid phase from the mixture, and purifying the binding pairs; and e) separating the cellular components from the binding pairs, wherein the guest compound-bound reactive compound is obtained through a covalent bond between a reactive compound and a guest compound represented by Formula 2 below, the host compound-bound solid phase is obtained through a covalent bond between a solid phase and a host compound represented by Formula 1 below, and the reactive compound includes at least one selected from the group consisting of a biomolecule, N-hydroxysuccimide, an antigen, an antibody, an aptamer, folic acid, transferrin, and any mixtures thereof:

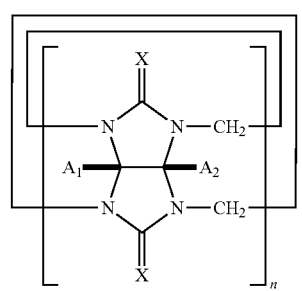

Formula 1 wherein n is an integer in the range of 6 to 10, X is one selected from the group consisting of O, S, and NH, $A_1$ and $A_2$ are each independently selected from the group consisting of H, OR, SR, NHR, COOH, $O(CH_2)_a S(CH_2)_b NH_2$, and $O(CH_2)_a S(CH_2)_b COOH$, wherein a and b are each independently an integer in the range of 1 to 5, R is selected from the group consisting of H, a $C_1$-$C_{30}$ alkyl group, a $C_2$-$C_{30}$ alkenyl group, a $C_2$-$C_{30}$ alkynyl group, a $C_2$-$C_{30}$ carbonylalkyl group, a $C_1$-$C_{30}$ thioalkyl group, a $C_1$-$C_{30}$ alkylthiol group, a $C_1$-$C_{30}$ hydroxyalkyl group, a $C_1$-$C_{30}$ alkylsilyl group, a $C_1$-$C_{30}$ aminoalkyl group, a $C_1$-$C_{30}$ aminoalkylthioalkyl group, a $C_5$-$C_{30}$ cycloalkyl group, a $C_2$-$C_{30}$ heterocycloalkyl group, a $C_6$-$C_{30}$ aryl group, a $C_7$-$C_{30}$ arylalkyl group, a $C_4$-$C_{30}$ heteroaryl group, and a $C_4$-$C_{30}$ heteroarylalkyl group, and both $A_1$ and $A_2$ are not hydrogen at the same time, $$A_3\text{-}B_1\text{-}A_4 \qquad \text{Formula 2}$$

wherein $A_3$ is a functional group forming a non-covalent bond with the host compound represented by Formula 1 and prepared by removing one atom from a terminal of one compound selected from the group consisting of adamantane, ferrocene, metallocene, carborane, cyclam, crown ether, amino acid, peptide, alkaloid, cisplatin, oxaliplatin, oligonucleotide, rhodamine, and nano particles, $A_4$ is a functional group selected from the group consisting of an amine group and a carboxyl group, $B_1$ includes at least one first functional group selected from the group consisting of —$(R_2O)_m$—, a $C_1$-$C_{20}$ alkylene group, a $C_2$-$C_{20}$ alkenylene group, a $C_2$-$C_{20}$ alkynylene group, a $C_5$-$C_{20}$ cycloalkylene group, a $C_6$-$C_{20}$ arylene group, a $C_4$-$C_7$ heteroarylene group, and a $C_1$-$C_{20}$ alkylsilylene group; and at least one second functional group selected from the group consisting of —N($R_1$)—, —C(=O)O—, —N($R_1$)C(=O)—, and —S—S—, wherein —N($R_1$)— is essential among the second functional groups, m is a real number in the range of 1 to 5, $R_2$ is a $C_1$-$C_3$ alkylene group, and $R_1$ is H or a $C_1$-$C_5$ alkyl group.

According to an aspect of the present invention, there is provided a kit including:

a host compound-bound solid phase; and a guest compound-bound reactive compound, wherein the host compound-bound solid phase is obtained through a covalent bond between a solid phase and a host compound represented by Formula 1 below, the guest compound-bound reactive compound is obtained through a covalent bond between a reactive compound and a guest compound represented by Formula 2 below, and the reactive compound includes at least one selected from the group consisting of a biomolecule, N-hydroxysuccimide, an antigen, an antibody, an aptamer, folic acid, transferrin, and any mixtures thereof.

BEST MODE FOR CARRYING OUT THE INVENTION

Figure 1:
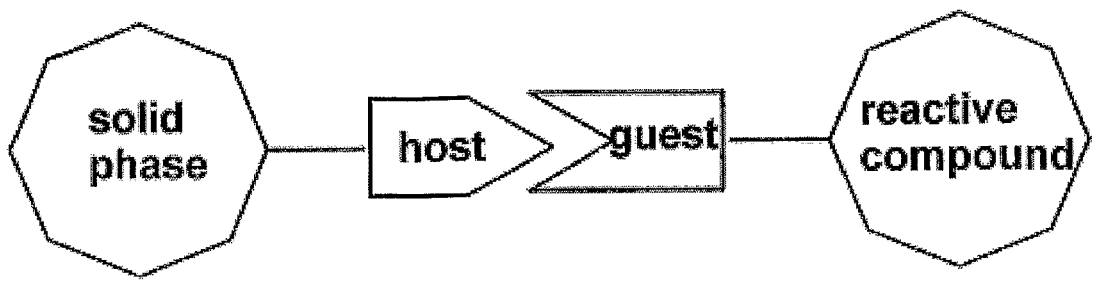
FIG. 1 schematically illustrates a non-covalent bond formed between a host compound bound to a solid phase and a guest compound bound to a reactive compound.

Hereinafter, the present invention will now be described more fully with reference to the accompanying drawings, in which exemplary embodiments of the invention are shown.

A method of separating cellular components according to an embodiment includes: a) contacting a guest compound-bound reactive compound with cells; b) lysing the cells; c) adding a host compound-bound solid phase to a solution including the lysates of the cells to prepare a mixture; d) separating binding pairs of the guest compound bound to cellular components and the host compound bound to the solid phase from the mixture and purifying the binding pairs; and e) separating the cellular components from the binding pairs, wherein the guest compound-bound reactive compound is obtained through a covalent bond between a reactive compound and a guest compound represented by Formula 2 below, the host compound-bound solid phase is obtained through a covalent bond between a solid phase and a host compound represented by Formula 1 below, and the reactive compound includes at least one selected from the group consisting of biomolecule, N-hydroxysuccimide, an antigen, an antibody, an aptamer, folic acid, transferrin, and any mixtures thereof:

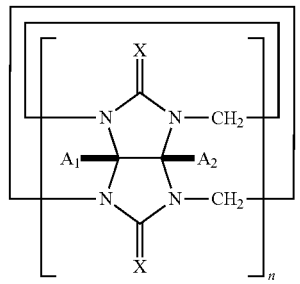

Formula 1 wherein n is an integer in the range of 6 to 10, and X is one selected from the group consisting of O, S, and NH, $A_1$ and $A_2$ are each independently selected from the group consisting of H, OR, SR, NHR, COOH, $O(CH_2)_a S(CH_2)_b NH_2$, and $O(CH_2)_a S(CH_2)_b COOH$, wherein a and b are each independently an integer in the range of 1 to 5, R is selected from the group consisting of H, a $C_1$-$C_{30}$ alkyl group, a $C_2$-$C_{30}$ alkenyl group, a $C_2$-$C_{30}$ alkynyl group, a $C_2$-$C_{30}$ carbonylalkyl group, a $C_1$-$C_{30}$ thioalkyl group, a $C_1$-$C_{30}$ alkylthiol group, a $C_1$-$C_{30}$ hydroxyalkyl group, a $C_1$-$C_{30}$ alkylsilyl group, a $C_1$-$C_{30}$ aminoalkyl group, a $C_1$-$C_{30}$ aminoalkylthioalkyl group, a $C_5$-$C_{30}$ cycloalkyl group, a $C_2$-$C_{30}$ heterocycloalkyl group, a $C_6$-$C_{30}$ aryl group, a $C_7$-$C_{30}$ arylalkyl group, a $C_4$-$C_{30}$ heteroaryl group, and a $C_4$-$C_{30}$ heteroarylalkyl group, and both $A_1$ and $A_2$ are not hydrogen at the same time, $$A_3\text{-}B_1\text{-}A_4 \qquad \text{Formula 2}$$

wherein $A_3$ is a functional group forming a non-covalent bond with the host compound represented by Formula 1 and prepared by removing one atom from a terminal of one compound selected from the group consisting of adamantane, ferrocene, metallocene, carborane, cyclam, crown ether, amino acid, peptide, alkaloid, cisplatin, oxaliplatin, oligonucleotide, rhodamine, and nano particles, $A_4$ is a functional group selected from the group consisting of an amine group and a carboxyl group, $B_1$ includes at least one first functional group selected from the group consisting of —$(R_2O)_m$—, a $C_1$-$C_{20}$ alkylene group, a $C_2$-$C_{20}$ alkenylene group, a $C_2$-$C_{20}$ alkynylene group, a $C_5$-$C_{20}$ cycloalkylene group, a $C_6$-$C_{20}$ arylene group, a $C_4$-$C_7$ heteroarylene group, and a $C_1$-$C_{20}$ alkylsilylene group; and at least one second functional group selected from the group consisting of —N($R_1$)—, —C(=O)O—, —N($R_1$)C(=O)—, and —S—S—, wherein —N($R_1$)— is essential among the second functional groups, m is a real number in the range of 1 to 5, $R_2$ is a $C_1$-$C_3$ alkylene group, and $R_1$ is H or a $C_1$-$C_5$ alkyl group. For example, $R_1$ may be a methyl group.

According to the method, cellular components may be simply and selectively separated from cells and purified since a host compound, which is selectively and covalently bound to a solid phase or cellular components, forms a non-covalent binding pair which is reversibly formed or disrupted according to conditions, with a guest compound.

In operation a), the guest compound-bound reactive compound is contacted with cells to bind to cellular components. The reactive compound may be a compound having a reactive group forming a covalent bond with the cellular components or a compound recognizing a specific cellular component. Cell membrane protein may be separated using the reactive compound forming a covalent bond with the cellular components. Specific proteins such as phospholipase (PLD), G-protein couples receptor (GPCR), protein kinase A (PKA), and Munc-18 may be separated using the reactive compound recognizing a specific cellular component. The guest compound represented by Formula 2 may be bound to various cellular components by applying an appropriate reactive compound.

In general, the guest compound of Formula 2 covalently bound to the reactive compound may be contacted with cells by adding the guest compound to a solution including the cells, but any method that is commonly used in the art may be used.

In operation b), the cells may be lysed by a cell lysis solution, but any method that is commonly used in the art may be used without limitation.

In operation c), the host compound may form a binding pair with the guest compound via a non-covalent bond by adding the host compound-bound solid phase to the guest compound solution. The formation of the binding pair may be identified in an IR absorption spectrum.

For example, the guest compound of Formula 2 may be inserted into a cavity of a cucurbituril derivative of Formula 1 to form a non-covalent bond. The formation of the non-covalent bond depends on the pH of the solution. In particular, the cucurbituril derivative, as the host compound of Formula 1, forms a binding pair with the guest compound of Formula 2 in an acidic solution. The binding pair is disrupted in a basic solution. In other words, under the conditions in which an amine group contained in the guest compound of Formula 2 is hydrogenised, the binding pair is formed. Under the conditions in which the amine group is dehydrogenised, the binding pair is disrupted. In a solution having a pH equal to or less than 8, a coupling constant of the cucurbituril derivative and the guest compound is in the range of about $10^{10}$ to about $10^{15}$ $M^{-1}$, so that most of the cucurbituril derivative is non-covalently bonded to the guest compound. However, in a solution having a pH greater than 8, the coupling constant of the cucurbituril derivative and the guest compound is in the range of about $10^0$ to about $10^4 M^{-1}$, so that most of the binding pair is dissociated. That is, as the pH of the solution is decreased, i.e., the solution becomes more acidic, the coupling constant of the cucurbituril derivative and the guest compound is increased. As the pH of the solution is increased, i.e., the solution becomes more basic, the coupling constant of the cucurbituril derivative and the guest compound is decreased.

For example, the coupling constant between cucurbituril derivative, constituting the host compound, (n=7) and adamantane amine or a ferrocene methylamine derivative, constituting the guest compound, may be equal to or greater than $10^{12}M^{-1}$ at a pH equal to or less than 8 so that the cucurbituril derivative is bound to the adamantane amine or the ferrocene methylamine derivative through a non-covalent bond. On the other hand, when the coupling constant is about equal to or less than $10^4 M^{-1}$ at a pH greater than 8, the binding pair is dissociated.

In operation d), the binding pair may be separated from the mixture and purified using any method commonly used in the art, for example, filtration, a method of using magnets. The separation and purification method may vary according to properties of the solid phase contained in the binding pair.

In operation e), the separated cellular components may be purified using an additional purification method such as dialysis.

The cellular components may include at least one selected from the group consisting of a cell membrane protein, an enzyme, a nucleic acid, a protein, an amino acid, an antibody, an antigen, an inhibitor, a vitamin, a cofactor, a fatty acid, a cell membrane, a substrate, a substrate analog, a suppressor, a coenzyme, a virus, lectin, a polysaccharide, a glycoprotein, a receptor, histone, an adenosine triphosphate (ATP), an adenosine diphosphate (ADP), a hormone receptor, and glutathione, but is not limited thereto. Any cellular component that has a terminal reactive functional group such as an amine group or a carboxyl group on the surface of the cellular component and may form a covalent bond with the reactive compound, or any cellular component that is recognized by the reactive compound may be used.

The biomolecule may include at least one selected from the group consisting of a cell membrane protein, an enzyme, a nucleic acid, a protein, an amino acid, an antibody, an antigen, an inhibitor, a vitamin, a cofactor, a fatty acid, a cell membrane, a substrate, a substrate analog, a suppressor, a coenzyme, a virus, lectin, a polysaccharide, a glycoprotein, a receptor, histone, an ATP, an ADP, a hormone receptor, and glutathione. That is, the cellular component may be the reactive compound. For example, when an antigen, among the cellular components, is bound to the guest compound and bound to an antibody, the antigen functions as a reactive compound. The biomolecule may have a terminal reactive functional group such as an amine group or a carboxyl group to form a covalent bond with the cellular components.

The enzyme may include one selected from the group consisting of cellulase, hemi-cellulase, peroxidase, protease, amylase, xylanase, lipase, esterase, cutinase, pectinase, keratinase, reductase, oxidase, phenoloxidase, lipoxygenase, ligninase, pullulanase, arabinosidase, hyaluronidase and any combinations thereof The solid phase may include at least one selected from the group consisting of a polymer, a magnetic bead, a polymer-coated magnetic bead, silica gel, agarose gel, polymer or gold-coated silica gel, a zirconium oxide, a monolithic polymer, gold thin film, silver thin film, glass, ITO-coated glass, silicon, metal electrode, nanorod, nanotube, nanowire, curdlan gum, cellulose, nylon membrane, sepharose, sephadex, and any mixtures thereof, for example agarose gel. The solid phase may have a terminal reactive functional group on the surface thereof. The terminal reactive functional group forms a covalent bond with the host compound of Formula 1. The terminal reactive functional group may include one selected from the group consisting of a halogen group, a cyano group, a carboxyl group, an amine group, a hydroxy group, an allyloxy group, a succinimidyl group, a thiol group, and any mixtures thereof. The solid phase may be in the form of beads.

The number of hydroxy groups contained in one molecule of the host compound represented by Formula 1 may be in the range of 1 to 14, for example, in the range of 5 to 6.

The host compound may be represented by one selected from the group consisting of Formulae 3 to 5 below.

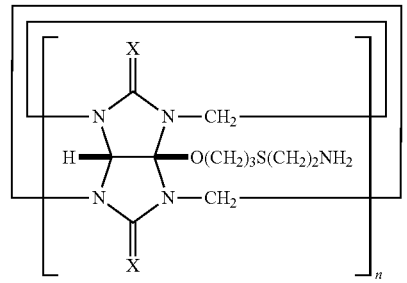

Formula 3

Formula 4

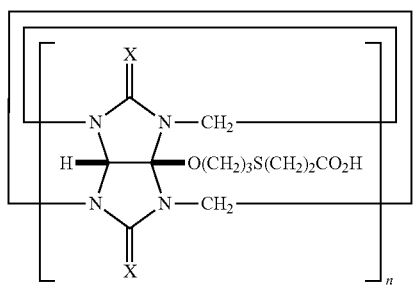

Formula 5

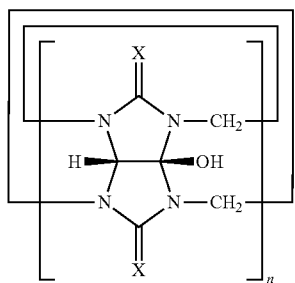

wherein n is an integer in the range of 6 to 10, and X is one selected from the group consisting of O, S, and NH.

In Formula 1, n may be 7, and X may be O. That is, the host compound may be a cucurbit[7]uril derivative.

The guest compound represented by Formula 2 may be represented by one selected from the group consisting of Formulae 6 to 9 below.

Formula 6

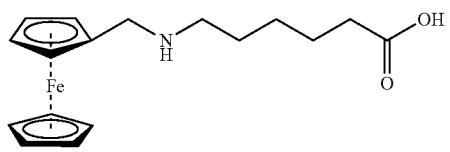

Formula 7

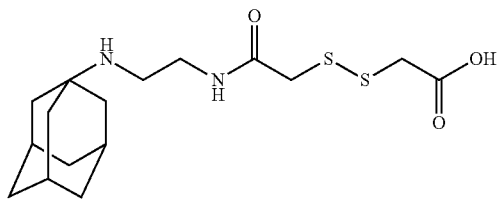

Formula 8

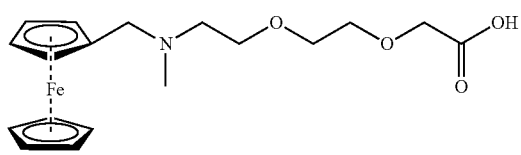

Formula 9

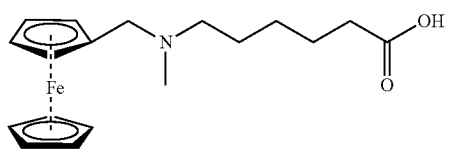

The guest compound represented by one of Formulae 6 to 9 is covalently bound to N-hydroxysuccimide or N-hydroxysuccimide sulfonate, constituting a reactive compound, to form a guest compound-bound reactive compound of operation a) represented by one of Formulae 11 to 13 below.

Formula 11

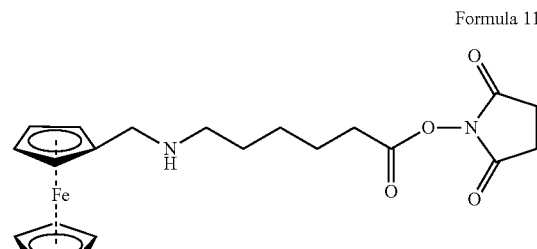

Formula 12

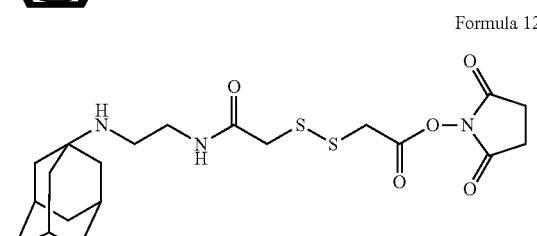

Formula 13

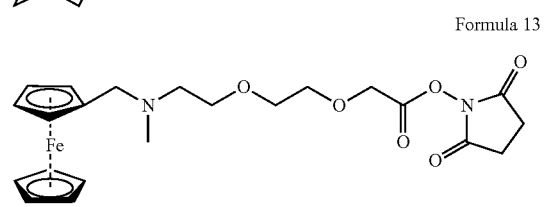

A cleaning solution used in the purification of operation d) may include at least one solvent selected from the group consisting of methanol, trifluoroacetic acid, triethylamine, methylene chloride, chloroform, dimethylformamide, dimethyl sulfoxide, toluene, acetonitrile, xylene, chloro benzene, tetrahydrofuran, diethyl ether, ethanol, diglycol ether, silicon oil, supercritical carbon dioxide, ionic liquid, N-methylpyrrolidine, pyridine, water, ammonium hydroxide, dioxane, chloroform, and any mixtures thereof.

A cleaning solution used in the purification of operation d) may include at least one solvent selected from the group consisting of tris-hydrochloric acid, sodium chloride, ethylenediaminetetraacetic acid (EDTA), sodium lauryl sulfate (SDS), triton X-100, triton x-114, tween-20, tween-80, Brij-35, Brij-58, octyl-beta-glucoside, 06 guaine transferase (OGT), CHAPS, CHAPSO, sodium oxycholate, nonidet P-40 (NP-40), protease inhibitor (PMSF), pyrophosphate, beta-glycerophosphate, sodium fluoride, potassium chloride, sodium vanadate, and any mixtures thereof.

A kit according to another embodiment includes: the host compound-bound solid phase; and the guest compound-bound reactive compound, wherein the host compound-bound solid phase is obtained through a covalent bond between a solid phase and the host compound represented by Formula 1 below, the guest compound-bound reactive compound is obtained through a covalent bond between a reactive compound and the guest compound represented by Formula 2 below, and the reactive compound may include at least one of the group consisting of a biomolecule, N-hydroxysuccimide, an antigen, an antibody, an aptamer, folic acid, transferrin, and any mixtures thereof.

In the kit, the biomolecule may include at least one of the group consisting of a cell membrane protein, an enzyme, a nucleic acid, a protein, an amino acid, an antibody, an antigen, an inhibitor, a vitamin, a cofactor, a fatty acid, a cell membrane, a substrate, a substrate analog, a suppressor, a coenzyme, a virus, lectin, a polysaccharide, a glycoprotein, a receptor, histone, an ATP, an ADP, a hormone receptor, and glutathione.

In the kit, the solid phase may include at least one of the group consisting of a polymer, a magnetic bead, a polymer-coated magnetic bead, silica gel, agarose gel, polymer or gold-coated silica gel, a zirconium oxide, a monolithic polymer, gold thin film, silver thin film, glass, ITO-coated glass, silicon, metal electrode, nanorod, nanotube, nanowire, curdlan gum, cellulose, nylon membrane, sepharose, sephadex, and any mixtures thereof.

In the kit, the host compound of Formula 1 may be represented by one selected from the group consisting of Formulae 3 to 5 below:

Formula 3

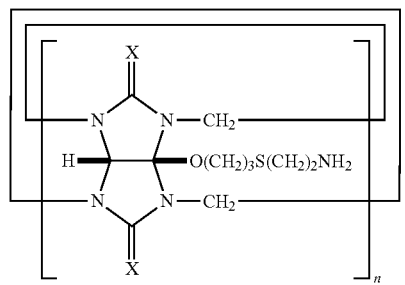

Formula 4

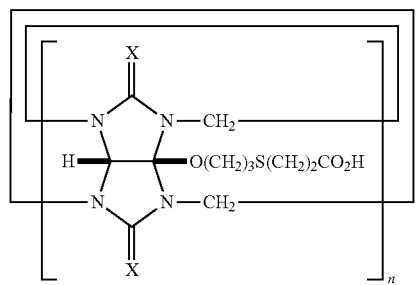

Formula 5

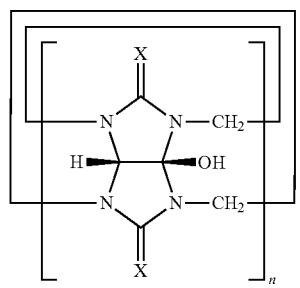

wherein n is an integer in the range of 6 to 10, and X is one selected from the group consisting of O, S, and NH.

In Formula 1, n may be 7 and X may be O.

The guest compound of Formula 2 may be represented by one selected from the group consisting of Formulae 6 to 9 below.

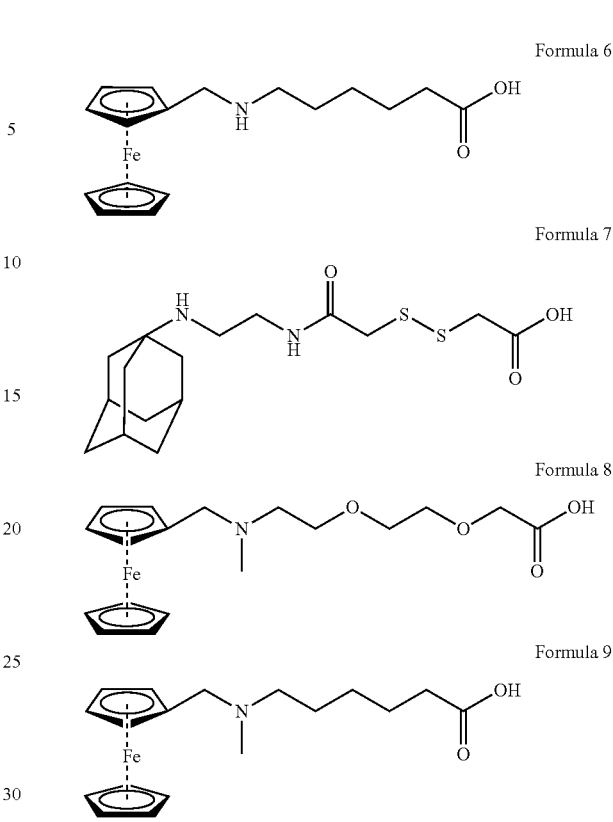

In the kit, the host compound, instead of the guest compound, may be bound to the reactive compound, and the guest compound, instead of the host compound, may be bound to the solid phase.

MODE FOR INVENTION

The present invention will be described in greater detail with reference to the following examples. The following examples are for illustrative purposes and are not intended to limit the scope of the invention.

Preparation Example 1

Figure 2:
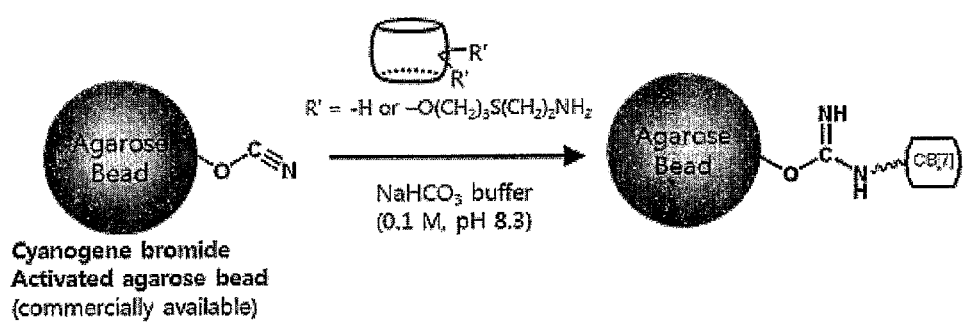
FIG. 2 schematically illustrates the fixation of monoamine cucurbit[7]uril to agarose beads according to Preparation Example 1.

Fixation of Host Compound (Monoamine Cucurbit[7]uril) to Solid Phase 10 mg of monoamine cucurbit[7]uril ($7.7 \times 10^{-3}$ mmol) was dissolved in 2 mL of a coupling buffer (0.1 M $NaHCO_3$, 0.5 M NaCl, pH 8.4). 0.5 g of cyanogen bromide activated agarose beads was added to an HCl (1 mM, 50 mL) water solution and swelled for 30 minutes. The mixture was centrifuged at a rate equal to or less than 400 rpm so that the beads were not damaged. The supernatant was removed, and 50 mL of distilled water was added thereto to clean the beads. The beads were added to a 4 mL vial, and 2 mL of a coupling buffer in which the monoamine cucurbit[7]uril is dissolved was added thereto. The resultant was left to sit at room temperature for 2 hours while slowly rotating. The resultant was centrifuged at a rate equal to or less than 400 rpm, the supernatant was removed, and the resultant was washed with the coupling buffer. 4 mL of ethanol amine (1 M) was added thereto and the mixture was left to sit at room temperature for 2 hours while slowing rotating to inactivate residing cyanogen groups. The resultant was washed with alternatively an acetate buffer (0.1M acetic acid, 0.5 M NaCl, pH 4) and the coupling buffer (5× each). FIG. 2 schematically illustrates the fixation process.

Preparation Example 2

Figure 8:
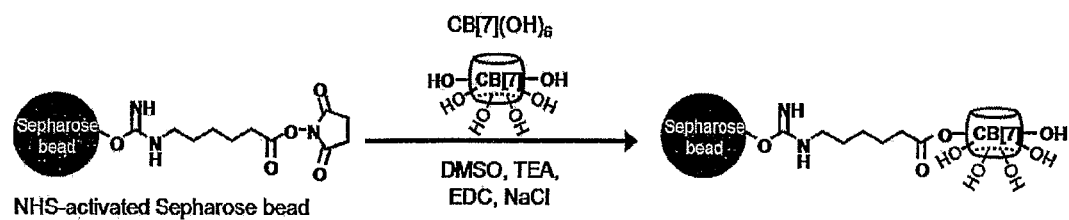
FIG. 8 schematically illustrates the fixation of hydroxy cucurbit[7]uril(CB[7](OH)$_6$) to N-hydroxysuccimidyl sepharose beads according to Preparation Example 2.

Fixation of Host Compound (Hydroxy Cucurbit[7]uril) to Solid Phase 1 ml of N-hydroxysuccimidyl sepharose beadsslurry (Sigma-Aldrich, H82820N-Hydroxysuccinimidyl-Sepharose® 4 Fast Flow) contained in isopropanol was washed with dimethyl sulfoxide (DMSO) to remove isopropanol. 276 mg of hydroxy cucurbit[7]uril (CB[7](OH)$_6$, 144 µmol), 88 mg of 1-ethyl-3-(3-dimethylaminopropyl)carbodiimide hydrochloride (460 µmol), and 50 mg of NaCl (850 µmol) were dissolved in 6 ml of DMSO, and the mixture was added to the beads with 1 ml of triethyl amine. The mixture was left to sit at room temperature for 48 hours while slowing rotating. The resultant was centrifuged at a rate equal to or less than 400 rpm, the supernatant was removed, and the resultant as washed with DMSO. Then, the resultant was washed with distilled water and a sodium chloride water solution (0.5M NaCl) (5× each). FIG. 8 schematically illustrates the fixation process.

Preparation Example 3

Synthesis of Guest Compound Bound to Reactive Compound

Ferrocene-N-hydroxysuccimide (Ferrocene-NHS)-Based Guest Compound

A guest compound bound to a reactive compound was prepared in the same manner as in C. Padeste, A. Grubelnik, L. Tiefenauer *Biosens. Bioelectron.* 2000, 15, 431. The guest compound bound to a reactive compound was prepared according to Reaction Scheme 1 below.

Reaction Scheme 1

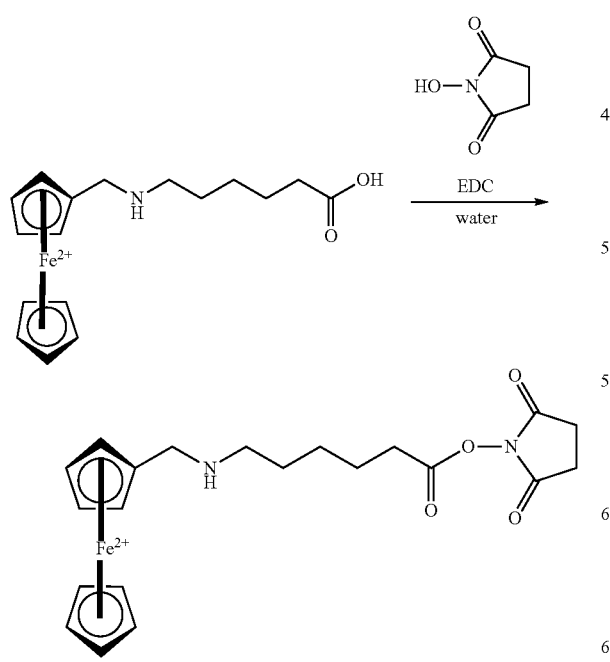

Preparation Example 4

Synthesis of Guest Compound Bound to Reactive Compound

Adamantane-N-Hydroxysuccimide (Adamantane-S—S—NHS)-Based Guest Compound 10 mg of N-(1-adamantayl)ethylenediamene (5.2×10$^{-2}$ mmol, TCI) and 28 mg of dithiodiglycolic acid (1.5×10$^{-1}$ mmol) were added to 5 mL of H$_2$O. 9.8 mg of 1-ethyl-3-(3-dimethylaminopropyl)carbodiimide hydrochloride (EDC, 5.2×10$^{-2}$ mmol, Aldrich) and 7.0 mg of N-Hydroxybenzotriazole (HOBt, 5.2×10$^{-2}$ mmol, Aldrich) were added thereto while stirring, and the mixture was stirred for 2 hours. The reactants were separated by size-exclusion chromatography using sephadex G-10 to obtain 10 mg of an intermediate compound (adamantane-S—S-carboxylic acid) (Yield: 54%).

$^1$-NMR (500 MHz, D2O): d=1.71-2.14 (m), 2.66 (t), 3.45 (S), 3.50 (m), 3.52 (m)

EI-Mass [M$^+$] calc.=358.1, found=358.1

Then, 10 mg of the intermediate compound (adamantane-S—S-carboxylic acid) (2.8×10$^{-2}$ mmol) was dissolved in 5 mL of H$_2$O, and 4 mg of N-hydroxysuccinimide (NHS, 3.5×10$^{-2}$ mmol, aldrich) was added thereto. Then, the mixture was stirred at room temperature for 2 hours to obtain a resultant (adamantane-S—S—NHS). The reaction mixture was directly used in Example 2 without a separation process. The intermediate compound and the resultant are shown in Reaction Scheme 2 below.

Reaction Scheme 2

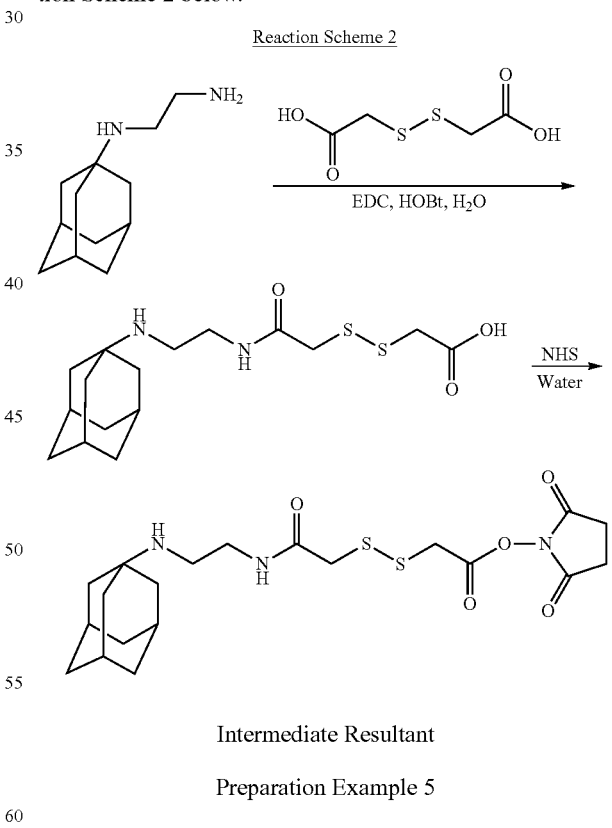

Intermediate Resultant

Preparation Example 5

Synthesis of Guest Compound Bound to Reactive Compound

Ferrocene-N-Methyl-Hydroxysuccimide (Ferrocene-N-Methyl-NHS)-Based Guest Compound 690 mg of ferrocene-aldehyde (3.2 mmol) was dissolved in 10 ml of DMF, 456 mg of 8-amino-3,6-dioxaoctanoic acid (2.8 mmol) dissolved in 2.5 ml of 2M NaOH was added thereto, and the mixture was stirred at 80° C. for 2 hours. The mixture was cooled to room temperature, 320 mg of NaBH$_4$ (8.4 mmol) dissolved in 2.5 ml of distilled water was added thereto, and the mixture was stirred for 12 hours. The pH of the mixture was adjusted to 5 by slowly adding acetic acid (10% in H$_2$O) to the mixture. A by-product such as Fc-CH$_2$OH and the residing 8-amino-3,6-dioxaoctanoic acid which did not react were subjected to extraction from the reactants using ethyl acetate. A H$_2$O phase was heated to 50° C. under a reduced pressure to reduce the volume, and the separation was performed by column chromatography using silica gel. N-(ferrocenylmethyl)-8-amino-3,6,-dioxaoctanoic acid was separated using an eluent of 30% MeOH in CHCl$_3$. (Yield: 42%); $^1$H NMR (CDCl$_3$, 500 MHz) δ: 2.99 (t, 2H, J=4.2 Hz), 3.58 (s like, 4H), 3.67 (t, 2H, J=4.2 Hz), 3.90 (s, 2H), 3.95 (s, 2H), 4.15 (s, 5H), 4.19 (s, 2H), 4.35 (s, 2H); $^{13}$C NMR (CD$_3$OD, 125 MHz) δ: 47.0, 67.0, 70.1 (5C), 70.7 (2C), 71.1, 71.2, 71.6, 71.7, 71.8 (2C), 76.7, 176.9; EIMS: 361 (M$^+$+1).

36 mg of N-(ferrocenylmethyl)-8-amino-3,6,-dioxaoctanoic acid (0.1 mmol) was dissolved in 2 mL of acetonitrile, 50 L of 30% formalin solution was added thereto, and the mixture was stirred for 30 minutes. NaBH$_3$CN was added thereto, and the mixture was further stirred for 30 minutes. Then, glacial acetic acid was added thereto to adjust the pH to 5. The mixture was stirred at room temperature for 12 hours. Excess distilled water was added thereto, and the mixture was stirred for 30 minutes. Then, the mixture was concentrated and the separation was performed using column chromatography. 20 mg of an intermediate compound (N-(ferrocenylmethyl)-N-methyl-8-amino-3,6,-dioxaoctanoic acid) was obtained in a 1:3 MeOH/CHCl$_3$ elution. (Yield: 55%) $^1$H NMR (CDCl$_3$, 500 MHz) δ: 2.61 (s, 3H), 3.01 (s like, 2H), 3.69-3.71 (m, 4H), 3.81 (s like, 2H), 4.02 (s, 2H), 4.14 (s, 5H), 4.20 (s, 2H), 4.27 (s, 2H), 4.35 (s, 2H); $^{13}$C NMR (CDCl$_3$, 125 MHz) δ: 39.4, 52.9, 55.7, 65.8, 69.0 (5C), 69.6 (2C), 69.9, 70.3 (2C), 70.8, 71.3 (2C), 175.6; EIMS: 375 (M$^+$+1).

Then, 10 mg of the intermediate compound (N-(ferrocenylmethyl)-N-methyl-8-amino-3,6,-dioxaoctanoic acid, 2.6×10$^{-2}$ mmol) was dissolved in 50 μL of DMF, and 4 mg of N-hydroxysuccimide (NHS, 3.5×10$^{-2}$ mmol, aldrich) and 6.6 mg of 1-ethyl-3-(3-dimethylaminopropyl)carbodiimide hydrochloride (EDC, 3.5×10$^{-2}$ mmol, aldrich) were added thereto. Then, the mixture was stirred at room temperature for 2 hours to obtain a resultant (Fc-NMe-PEG-NHS). The resultant was directly used in Example 4 without a separation process. The intermediate compound and the resultant are shown in Reaction Scheme 3 below.

Reaction Scheme 3

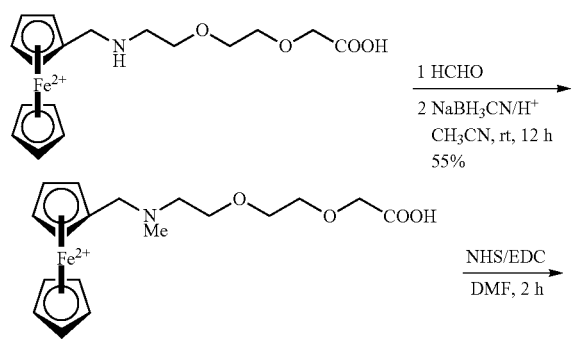

<intermediate compound>

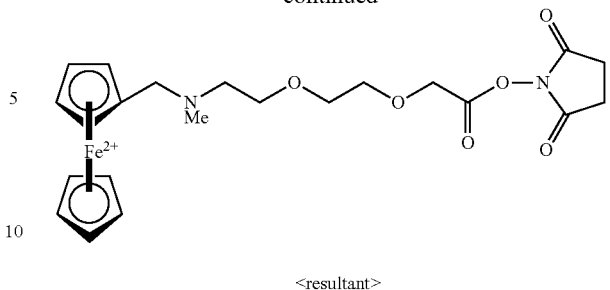

<resultant>

Preparation Example 6

Formation of Binding Pair of Guest Compound and Antibody (Anti-Munc18)

2.0 mg of a guest compound (ferrocene-NHS ligand) (4.5×10$^{-3}$ mmol) synthesized according to Preparation Example 3 was mixed with 1 mL of an antibody (anti-munc18, 0.1 mg/l mL), and the mixture was rotated at 4° C. for 4 hours. The formed guest compound-antibody binding pair was purified by dialysis. The formation of a ligand-antibody binding pair was identified using an infrared (IR) spectrophotometer. The binding pair was used in Example 3.

Example 1

Purification of Cell Membrane Protein (Using Ferrocene-N-Hydroxysuccimide(Ferrocene-NHS)-Based Guest Compound)

HEK293 cells were cultured in a plate, and a culture medium was removed. The cells were washed with 5 mL of ice-cold phosphate buffered saline (PBS) twice to completely remove the culture medium. 2.0 mg of the guest compound (3.8×10$^{-3}$ mmol) prepared according to Preparation Example 3 was dissolved in 5 mL of PBS, and the solution was added to the plate containing HEK293 cells. The cells were incubated at 4° C. for 30 minutes to induce a covalent bond between the guest compound and protein of the surface of the cells. Then, PBS including the guest compound was completely removed from the plate, and the remaining guest compound which was not bound to the protein was removed by adding fresh PBS. 0.1 M glycine solution was added to the plate and incubated at 4° C. for 30 minutes to inactivate the remaining guest compound. Then, 0.1 M glycine solution was removed, and the resultant was washed with PBS.

Figure 3:
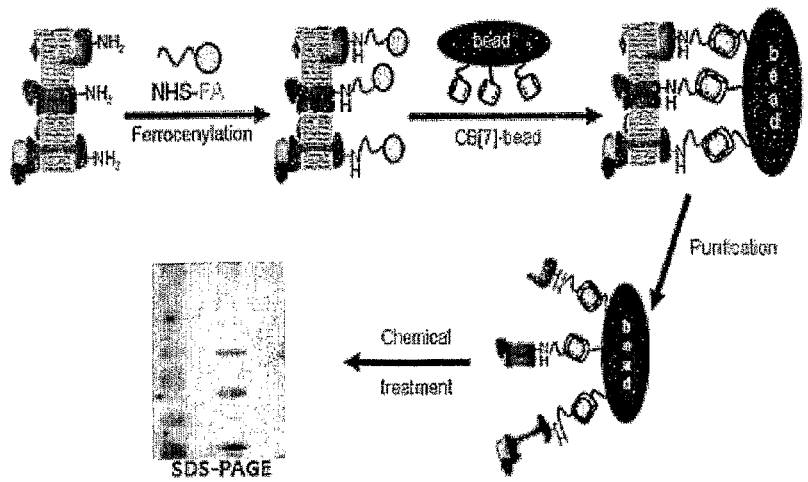
FIG. 3 schematically illustrates the separation and the purification of cellular components according to Example 1.
Figure 4:
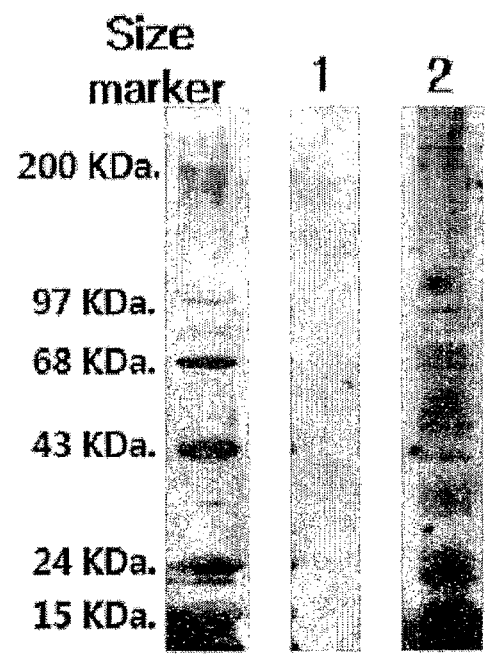
FIG. 4 illustrates results of cell membrane protein separated and purified according to Example 1 and Comparative Example 1 using SDS-PAGE.

Then, a cell lysis solution (1 mL, 10 mM Tris-HCl, 150 mM NaCl, 1 mM EDTA, 0.1% SDS, 1% Tx-100, 1% sodium deoxycholate) was added to the plate including the HEK293 cells. The solution of the plate including the lysates of the cells was harvested in s 1.5 mL tube. The cell lysates were sonicated. Then, the resultant was centrifuged at 14000 rpm, and 0.7 mL of the resulting supernatant was collected. 40 μL of monoamine cucurbit[7]uril-agarose beads prepared according to Preparation Example 1 was added to the separated supernatant, and the mixture was slowly rotated at 4° C. for 4 hours. The mixture was centrifuged at 1000 rpm to remove the supernatant, and the resulting beads were washed five times with the cell lysis solution. 30 μL of 2× sample buffer was added to the washed agarose beads, and the mixture was heated at 95° C. for 5 minutes to separate protein from the beads. The protein was separated using sodium dodecylsulfate polyacrylamide gel phoresis (SDS-PAGE) and sorted according to the size of the protein. FIG. 3 schematically illustrates the separation process. The protein separated according to Example 1 is shown in lane 2 of FIG. 4.

Example 2

Purification of Cell Membrane Protein (Adamantane-N-Hydroxysuccimide(Adamantane-S—S—NHS)-Based Guest Compound)

Figure 5:
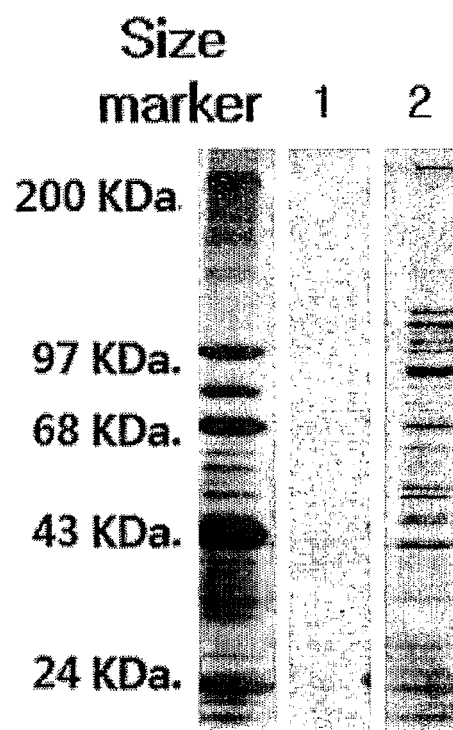
FIG. 5 illustrates results of cell membrane protein separated and purified according to Example 2 and Comparative Example 2 using SDS-PAGE.

HEK293 cells were cultured in a plate, and a culture medium was removed. The cells were washed with 5 mL of ice-cold phosphate buffered saline (PBS) twice to completely remove the culture medium. 3.0 mg of the guest compound ($4.4 \times 10^{-3}$ mmol) including a disulfide bond prepared according to Preparation Example 4 was dissolved in 5 mL of PBS, and the solution was added to the plate containing HEK293 cells. The cells were incubated at 4° C. for 30 minutes to induce a covalent bond between a ligand and protein of the surface of the cells. Then, PBS including the guest compound was completely removed from the plate, and the remaining guest compound which was not bound to the protein was removed by adding fresh PBS. 0.1 M glycine solution was added to the plate and incubated at 4° C. for 30 minutes to inactivate the remaining guest compound. Then, 0.1 M glycine solution was removed, and the resultant was washed with PBS. Then, a cell lysis solution (1 mL, 10 mM Tris-HCl, 150 mM NaCl, 1 mM EDTA, 0.1% SDS, 1% Tx-100, 1% sodium deoxycholate) was added to the plate including the HEK293 cells. The solution of the plate including the lysates of the cells was harvested in a 1.5 mL tube. The cell lysates were sonicated. Then, the resultant was centrifuged at 14000 rpm, and 0.7 mL of the resulting supernatant was collected. 40 μL of monoamine cucurbit[7]uril-agarose beads prepared according to Preparation Example 1 was added to the separated supernatant, and the mixture was slowly rotated at 4° C. for 4 hours. The mixture was centrifuged at 1000 rpm to remove the supernatant, and the resulting beads were washed five times with the cell lysis solution. 40 μL of DTT solution (1 mM) was added to the washed agarose beads to induce reduction of the disulfide bond contained in the ligand. 20 μL of the supernatant was mixed with 5 μL of 5× sample buffer, and the mixture was heated at 95° C. for 5 minutes. The protein was separated using SDS-PAGE and sorted according to the size of the protein. FIG. 3 schematically illustrates the separation process. The protein separated according to Example 2 is shown in lane 2 of FIG. 5.

Example 3

Purification of Antigen (Munc18)

Figure 6:
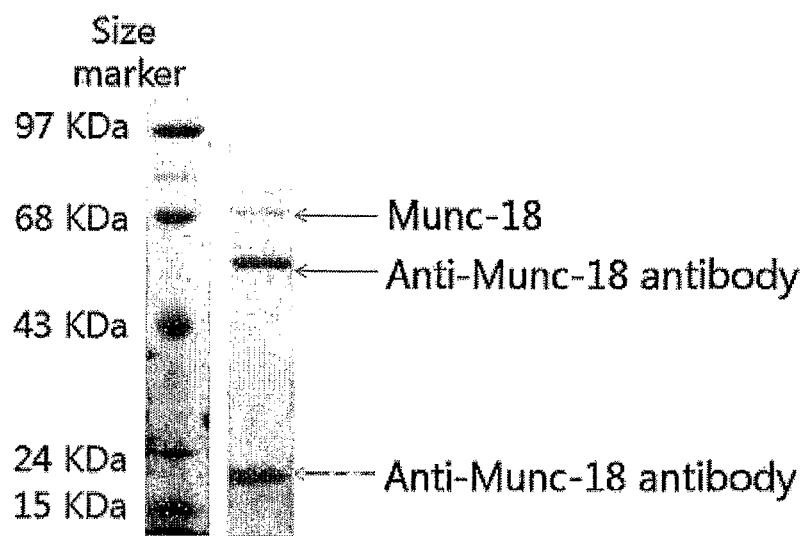
FIG. 6 illustrates results of antigen (Munc-18) separated and purified according to Example 3 using SDS-PAGE.

PC12 cells were cultured in a plate, and a culture medium was removed. The cells were washed twice with 5 mL of ice-cold phosphate buffered saline (PBS) to completely remove the culture medium. A cell lysis solution (1 mL, 10 mM Tris-HCl, 150 mM NaCl, 1 mM EDTA, 0.1% SDS, 1% Tx-100, 1% sodium deoxycholate) was added to the plate including the PC12. The solution of the plate including the lysates of the cells was harvested in a 1.5 mL tube. The cell lysates were sonicated. Then, the resultant was centrifuged at 14000 rpm, and 0.7 mL of the resulting supernatant was collected. 30 μL of the guest compound-antibody complex prepared according to Preparation Example 6 was added to the supernatant, and the mixture was slowly rotated at 4° C. for 24 hours. 40 μL of monoamine cucurbit[7]uril-agarose beads prepared according to Preparation Example 1 was added thereto, and the mixture was slowly rotated at 4° C. for 4 hours. The mixture was centrifuged at 1000 rpm to remove the supernatant, and the resulting beads were washed five times with the cell lysis solution. 30 μL of 2× sample buffer was added to the washed agarose beads, and the mixture was heated at 95° C. for 5 minutes to separate protein from the beads. It was identified that the purified protein using SDS-PAGE was an antigen (Munc18) having a size of 68 KDa in FIG. 6.

Example 4

Purification of Cell Membrane Protein

Ferrocene-N-Methyl-Hydroxysuccimide(Ferrocene-N-Methyl-NHS)-Based Compound

HEK293 cells were cultured in a plate, and a culture medium was removed. The cells were washed with 5 mL of ice-cold phosphate buffered saline (PBS) twice to completely remove the culture medium. 2.0 mg of the guest compound ($4.2 \times 10^{-3}$ mmol) prepared according to Preparation Example 5 was dissolved in 5 mL of PBS, and the solution was added to the plate containing HEK293 cells. The cells were incubated at 4° C. for 30 minutes to induce a covalent bond between the guest compound and protein of the surface of the cells. Then, PBS including the guest compound was completely removed from the plate, and the remaining guest compound which was not bound to the protein was removed by adding fresh PBS. 0.1 M glycine solution was added to the plate and incubated at 4° C. for 30 minutes to inactivate the remaining guest compound. Then, 0.1 M glycine solution was removed, and the resultant was washed with PBS.

Figure 7:
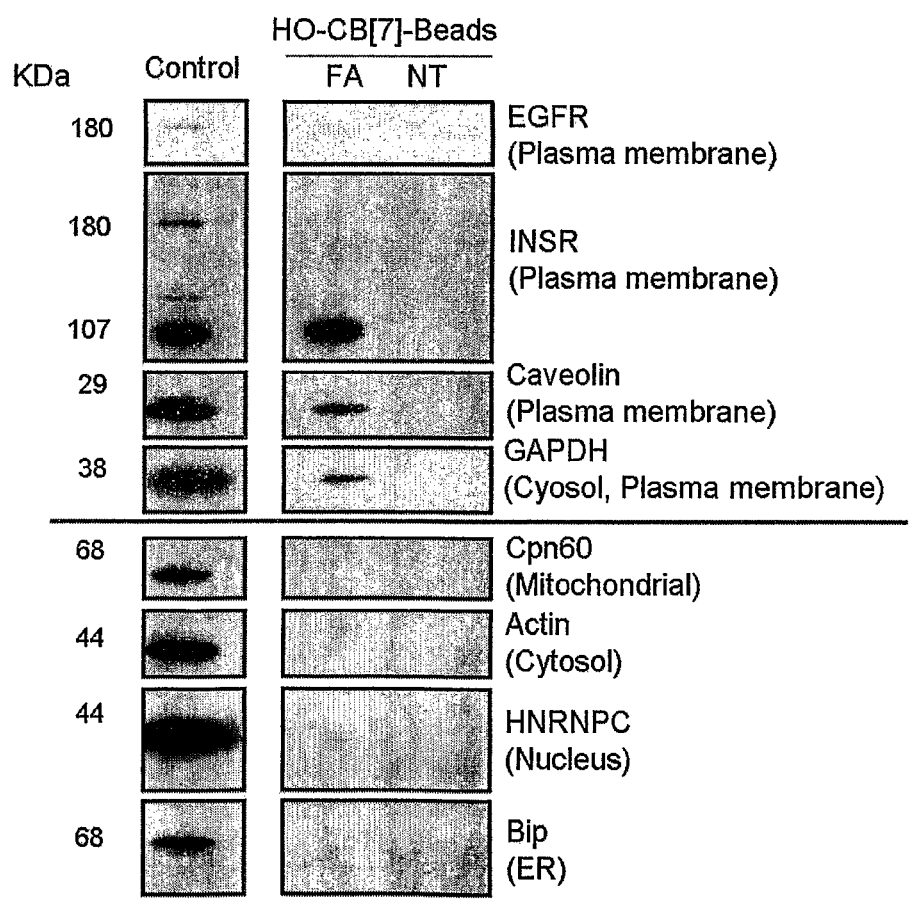
FIG. 7 illustrates immunoblotting results of cell membrane protein separated and purified according to Example 4 and Comparative Example 3.

Then, a cell lysis solution (RIPA buffer, 1 mL, 10 mM Tris-HCl, 150 mM NaCl, 1 mM EDTA, 0.1% SDS, 1% Tx-100, 1% sodium deoxycholate) was added to the plate including the HEK293 cells. The solution of the plate including the lysates of the cells was harvested in a 1.5 mL tube. The cell lysates were sonicated. Then, the resultant was centrifuged at 14000 rpm, and 0.7 mL of the resulting supernatant was collected. 40 μL of hydroxy cucurbit[7]uril-sepharose beads prepared according to Preparation Example 2 was added to the separated supernatant, and the mixture was slowly rotated at 4° C. for 4 hours. The mixture was centrifuged at 1000 rpm to remove the supernatant, and the resulting beads were washed five times with the cell lysis solution. 30 μL of 2× sample buffer was added to the washed sepharose beads, and the mixture was heated at 95° C. for 5 minutes to separate protein from the beads. The protein was separated using SDS-PAGE and sorted according to the size of the protein. FIG. 3 schematically illustrates the separation process. Then, the protein was transferred to a polyvinylidene fluoride membrane. Then, immunoblotting of the protein shown in FIG. 7 was performed using an antibody. Referring to FIG. 7, the cell membrane protein was selectively recovered while contamination by other cell organelle protein was minimized The control of the left lane in FIG. 7 shows the original amount of the protein contained in the cell lysis solution before the incubation with beads. The HO-CB[7]-beads of the right lane in FIG. 7 shows the amount of protein recovered after the incubation of the HO-CB[7]-beads with the cell lysis solution.

In FIG. 7, FA indicates the result of using the ferrocene-based guest compound, and NT indicates the result without using the ferrocene-based guest compound.

Locations of the proteins shown in FIG. 7 are shown in brackets under the names of the proteins.

Comparative Example 1

Purification of Cell Membrane Protein (Using Ferrocene-N-Hydroxysuccimide(Ferrocene-NHS-Based Guest Compound)

A cell membrane protein was separated in the same manner as in Example 1, except that HEK293 cells which were not contacted with the guest compound were used. The protein separated according to Comparative Example 1 is shown in lane 1 of FIG. 4.

Comparative Example 2

Purification of Cell Membrane Protein (Adamantane-N-Hydroxysuccimide(Adamantane-S—S—NHS)-Based Guest Compound)

A cell membrane protein was separated in the same manner as in Example 2, except that a solution including lysates of HEK293 cells which were not contacted with the guest compound were used. The protein separated according to Comparative Example 2 is shown in lane 1 of FIG. 5.

Comparative Example 3

Purification of Cell Membrane Protein (Using Ferrocene-N-Methyl-Hydroxysuccimide(Ferrocene-N-Methyl-NHS)-Based Guest Compound)

A cell membrane protein was separated in the same manner as in Example 4, except that HEK293 cells which were not contacted with the guest compound were used. The protein separated according to Comparative Example 3 is shown in the right column (NT) of FIG. 7.

As shown in the examples and the comparative examples, cellular components may be simply and selectively separated according to the method according to the present invention.

While the present invention has been particularly shown and described with reference to exemplary embodiments thereof, it will be understood by those of ordinary skill in the art that various changes in form and details may be made therein without departing from the spirit and scope of the present invention as defined by the following claims.

The invention claimed is:

1. A method of separating cellular components, the method comprising:
   a) contacting a guest compound-bound reactive compound with cells;
   b) binding the guest compound-bound reactive compound to a cellular component of the cell;
   c) lysing the cells;
   d) adding a host compound-bound solid phase to a solution comprising the lysates of the cells to prepare a mixture;
   e) separating binding pairs of the guest compound bound to cellular components and the host compound bound to the solid phase from the mixture, and purifying the binding pairs; and
   f) separating the cellular components from the binding pairs,
   wherein the host compound-bound solid phase is obtained through a covalent bond between a solid phase and a host compound represented by Formula 1 below,

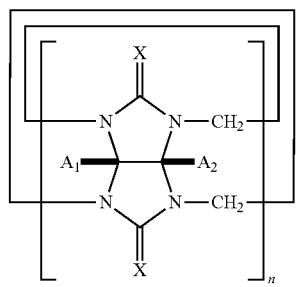

Formula 1 wherein n is an integer in the range of 6 to 10, X is one selected from the group consisting of O, S, and NH, $A_1$ and $A_2$ are each independently selected from the group consisting of H, OR, SR, NHR, COOH, $O(CH_2)_aS(CH_2)_bNH_2$, and $O(CH_2)_aS(CH_2)_bCOOH$, wherein a and b are each independently an integer in the range of 1 to 5, R is selected from the group consisting of H, a $C_1$-$C_{30}$ alkyl group, a $C_2$-$C_{30}$ alkenyl group, a $C_2$-$C_{30}$ alkynyl group, a $C_2$-$C_{30}$ carbonylalkyl group, a $C_1$-$C_{30}$ thioalkyl group, a $C_1$-$C_{30}$ alkylthiol group, a $C_1$-$C_{30}$ hydroxyalkyl group, a $C_1$-$C_{30}$ alkylsilyl group, a $C_1$-$C_{30}$ aminoalkyl group, a $C_1$-$C_{30}$ aminoalkylthioalkyl group, a $C_5$-$C_{30}$ cycloalkyl group, a $C_2$-$C_{30}$ heterocycloalkyl group, a $C_6$-$C_{30}$ aryl group, a $C_7$-$C_{30}$ arylalkyl group, a $C_4$-$C_{30}$ heteroaryl group, and a $C_4$-$C_{30}$ heteroarylalkyl group, and both $A_1$ and $A_2$ are not hydrogen at the same time, and wherein the guest compound-bound reactive compound is a compound selected from a group consisting of Formulae 12 and 13 below:

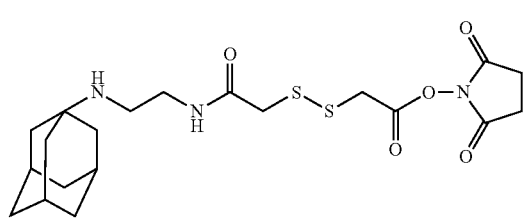

Formula 12

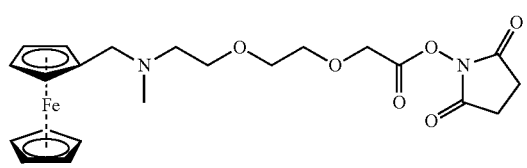

Formula 13

2. The method of claim 1, wherein the cellular components comprise at least one selected from the group consisting of a cell membrane protein, an enzyme, a nucleic acid, a protein, an amino acid, an antibody, an antigen, an inhibitor, a vitamin, a cofactor, a fatty acid, a cell membrane, a substrate, a substrate analog, a suppressor, a coenzyme, a virus, lectin, a polysaccharide, a glycoprotein, a receptor, histone, an adenosine triphosphate (ATP), an adenosine diphosphate (ADP), a hormone receptor, glutathione, and any mixtures thereof.

3. The method of claim 1, wherein the solid phase comprises at least one selected from the group consisting of a polymer, a magnetic bead, a polymer-coated magnetic bead, silica gel, agarose gel, polymer or gold-coated silica gel, a zirconium oxide, a monolithic polymer, gold thin film, silver thin film, glass, ITO-coated glass, silicon, metal electrode, nanorod, nanotube, nanowire, curdlan gum, cellulose, nylon membrane, sepharose, sephadex, and any mixtures thereof.

4. The method of claim 1, wherein the host compound is covalently bonded to the solid phase through a terminal reactive functional group on the surface of the solid phase.

5. The method of claim 4, wherein the terminal reactive functional group comprises at least one selected from the group consisting of a halogen group, a cyano group, a carboxyl group, an amine group, a hydroxy group, an allyloxy group, a succinimidyl group, a thiol group, and any mixtures thereof.

6. The method of claim 1, wherein the solid phase is in the form of beads.

7. The method of claim 1, wherein the number of hydroxy groups included in the host compound represented by Formula 1 is in the range of 1 to 14.

8. The method of claim 1, wherein the host compound is represented by one selected from the group consisting of Formulae 3 to 5 below:

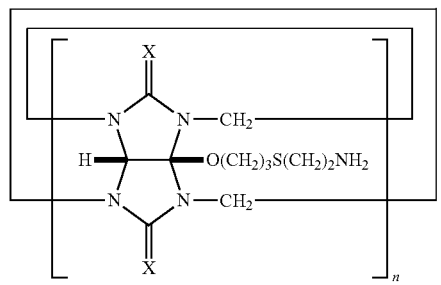

Formula 3

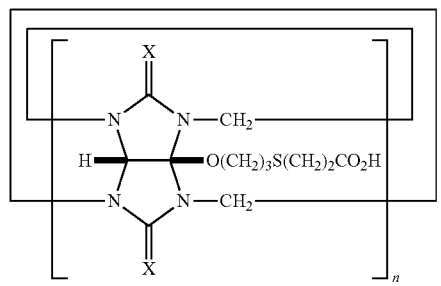

Formula 4

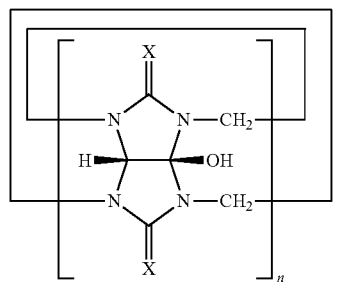

Formula 5 wherein n is an integer in the range of 6 to 10, and X is one selected from the group consisting of O, S, and NH.

9. The method of claim 1, wherein n is 7, and X is O in Formula 1.

10. The method of claim 1, wherein the guest compound is represented by one selected from the group consisting of Formula 7 and 8 below:

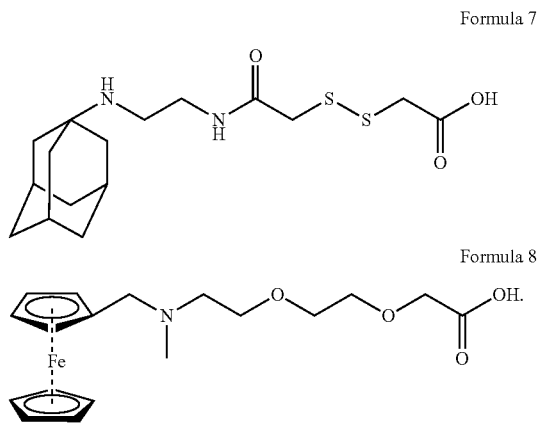

Formula 7

Formula 8

11. The method of claim 1, further comprising separating a disulfide bond of the guest compound using a reducing agent between operations e) and f).

12. The method of claim 1, wherein the separating the cellular components is performed by applying a basic aqueous solution to the binding pair in operation f).

13. The method of claim 1, wherein the separating the cellular components is performed by applying a guest compound aqueous solution to the binding pair in operation f).

14. The method of claim 1, wherein, in the purification of operation e), a cleaning solution used comprises at least one solvent selected from the group consisting of methanol, trifluoroacetic acid, triethylamine, methylene chloride, chloroform, dimethylformamide, dimethyl sulfoxide, toluene, acetonitrile, xylene, chloro benzene, tetrahydrofuran, diethyl ether, ethanol, diglycol ether, silicon oil, supercritical carbon dioxide, ionic liquid, N-methylpyrrolidine, pyridine, water, ammonium hydroxide, dioxane, chloroform, and any mixtures thereof.

15. The method of claim 1, wherein, in the purification of operation d), a cleaning solution used comprises at least one selected from the group consisting of tris-hydrochloric acid, sodium chloride, ethylenediaminetetraacetic acid (EDTA), sodium lauryl sulfate (SDS), t-octylphenoxypolyethoxyethanol, octylphenoxy polyethoxyethanol, polysorbate 20, polysorbate 80, polyethylene glycol dodecyl ether, polyethylene glycol hexadecyl ether, octyl-beta-glucoside, O6 guanine transferase (OGT), CHAPS, CHAPSO, sodium oxycholate, phenylmethylsulfonyl fluoride, pyrophosphate, beta-glycerophosphate, sodium fluoride, potassium chloride, and sodium vanadate.

* * * * *